United States Patent [19]

Nies

[11] Plant 4,431

[45] Jun. 26, 1979

[54] CHERRY TREE

[76] Inventor: Marvin L. Nies, 9296 E. Kettleman La., Lodi, Calif. 95240

[21] Appl. No.: 933,738

[22] Filed: Aug. 14, 1978

[51] Int. Cl.[2] ..... A01H 5/03

[52] U.S. Cl. ..... Plt./37

[58] Field of Search ..... Plt./37

*Primary Examiner*—Robert E. Bagwill

*Attorney, Agent, or Firm*—Roger B. Webster

[57] ABSTRACT

A cherry tree which is large, vigorous, upright to spreading, dense, vase-formed, hardy, foliated with large, ovate, abruptly acuminate, acutely pointed leaves having a crenate, finely serrate margin, medium length petiole, and large, mixed, red glands which are glabrous, compressed, opposite-alternate, and variable in number, blooms early-medium from hardy, medium size, medium length, conic, plump, free flower buds, the flowers being of medium size and white, and is a regular and very productive bearer of large, uniform, symmetrical, semi-freestone fruit having glassy, red skin, and red flesh having lighter streaking radiating from the pit cavity, the pit cavity being a darker red.

1 Drawing Figure

BACKGROUND OF THE VARIETY

1. Field of the Invention

The present variety of cherry tree resulted from a plant breeding program which is conducted by me in my experimental orchard located near Lodi, County of San Joaquin, Calif.; and the purpose of which program is the development of new and distinct varieties of cherry trees especially adapted to commercial growing. The present variety of cherry tree is embraced by Subclass 37, Plants, of the U.S. Patent Office MANUAL OF CLASSIFICATION.

2. Prior Varieties

Among the existent varieties of cherry trees which are known to me are those mentioned herein; to-wit, Mahaleb (unpatented), Hardy Giant (U.S. Plant Pat. No. 764), and Bing (unpatented).

ORIGIN OF THE VARIETY

The present variety of cherry tree was originated by me, in my experimental orchard located as aforesaid, as a controlled cross of Hardy Giant X Bing; the resultant seedling tree, when grown to maturity, evidenced novel and distinctive characteristics, and I, therefore, selected it for asexual reproduction preparatory to ultimate commercial growing thereof.

ASEXUAL REPRODUCTION OF THE VARIETY

The present variety of cherry tree was asexually reproduced by me, in my said experimental orchard, by budding on Mahaleb rootstock, and, in maturity, such asexual reproductions ran true to the original tree in all respects.

SUMMARY OF THE VARIETY

The herein-claimed new and distinct variety of cherry tree is large, vigorous, upright to spreading, dense, vase-formed, hardy, foliated with large, ovate, abruptly acuminate, acutely pointed leaves having a crenate, finely serrate margin, medium length petiole, and large, mixed, red glands which are glabrous, compressed, opposite-alternate, and variable in number, blooms early-medium from hardy, medium size, medium length, conic, plump, free flower buds, the flowers being of medium size and white, and is a regular and very productive bearer of large, uniform, symmetrical, semi-freestone fruit having glassy, red skin, and red flesh having lighter streaking radiating from the pit cavity, the pit cavity being a darker red.

The herein-claimed new and distinct variety of cherry tree is characterized, in particular comparison to the Bing, essentially as follows:

TREE STRUCTURE AND FOLIATION

The tree is slightly more vigorous with more lateral branching and longer lateral branches; the leafing time is approximately four days earlier, with leaves which are broader, not as acuminate, and some leaves are slightly cordate with a slight sinus at the point of petiole attachment, the margin being more crenate, and the glands being larger, mixed, more pigmented (very red on the terminals of the shoots), and usually in greater number. Additionally, there is much heavier pubescence on the bottom of new leaves, with the hairs persisting in larger amount on older leaves. The petioles have more dark red pigmentation, and young leaves on shoot tips are more bronze.

FLOWERING

The time of bloom is approximately four days earlier, and the flower—while similar to the Bing—has shorter sepals and a more globose torus. The sepals extend approximately one-half the distance to the base of the torus and reflex tightly against the torus. The sepals are crenate, while the sepals of Bing extend almost to the base of the torus and are acute (very slightly crenate at tip) not reflexing significantly against the torus. Also, the torus of the Bing is more elongated and narrower. The stamens exist in larger number and they reflex further outward; and the petals are wider and touch or overlap.

FRUIT

The fruit—which ripens more evenly and approximately six days earlier than the Bing—sizes larger and holds to size with large crops; is of a more attractive glassy appearance; sugar is higher earlier and can be eaten speckle ripe; acid is mild and enhances eating quality of greener fruit; and the fruit is wider and more globose in cross section. Additionally, the fruit rarely doubles, and in seasons when fruit of the Bing doubles extensively, the fruit of approximately thirty percent of the present variety has only a small suture extending from the base about one-quarter the distance toward the apex on the ventral side.

BRIEF DESCRIPTION OF THE DRAWING

The drawing is an illustration, by photographic reproduction in color, of a twig with leaves and fruit, and detached fruit; one of the latter being partially cut away to expose the flesh and stone.

DESCRIPTION OF THE VARIETY

The botanical details of this new and distinct variety of cherry tree—with color definitions (except those in common color terms) referenced to Maerz and Paul Dictionary of Color—are as follows:

Tree:
- *Size.*—Large.
- *Vigor.*—Vigorous.
- *Growth.*—Upright — spreading.
- *Density.*—Dense.
- *Form.*—Vase-formed.
- *Hardiness.*—Hardy.
- *Production.*—Very productive.
- *Bearing.*—Regular bearer.

Trunk:
- *Size.*—Stocky.
- *Texture.*—Medium.

Branches:
- *Size.*—Stocky.
- *Texture.*—Medium.
- *Color.*—Gray; dull.
- *Lenticels.*—Number: Few. Size: Small.

Leaves:
- *Size.*—Large. Average length — 14.6 cm. Average width — 7.6 cm.
- *Form.*—Ovate. Abruptly acuminate. Acutely pointed.
- *Thickness.*—Thick.
- *Color.*—Top side — Dark green (23-L-9). Under side — Lighter green (22-L-7).
- *Texture.*—Smooth.
- *Margin.*—Crenate. Finely serrate.
- *Petiole.*—Medium length. Medium thickness.
- *Glands.*—Number — very variable — usually 4 — sometimes as many as 7. Glabrous. Compressed. Alternate, sometimes opposite. Large. Mixed. Red. Positioned on petiole adjacent base of blade.
- *Stipules.*—2 — 1 on each side of petiole.

Flower buds:
- *Hardiness.*—Hardy.
- *Size.*—Medium.
- *Length.*—Medium.
- *Form.*—Conic. Plump. Free.

Flowers:
- *Date of bloom.*—Mar. 18th, 1978. Early — medium, compared with other varieties.
- *Size.*—Medium.
- *Color.*—White.

Fruit:
- *Maturity when described.*—Eating ripe — May 10th, 1978.
- *Date of first picking.*—May 10th, 1978.
- *Date of last picking.*—May 18th, 1978.
- *Size.*—Uniform. Large. Average diameter axially — 2.7 cm. Average transversely in suture plane — 2.4 cm.
- *Form.*—Uniform. Symmetrical transversely of the suture plane, but asymmetrical in the suture plane. Globose — oblate. Compressed in the suture plane.
- *Suture.*—Shallow. Inconspicuous. Extends from base to beyond apex.
- *Ventral surface.*—Rounded strongly just below base one-half distance to apex on suture line.
- *Cavity.*—Flaring. Rounded. Elongated in suture plane. Average depth — 3.25 mm. Average breadth — 4 mm. Color. — dark red.
- *Base.*—Rounded. Truncate.
- *Apex.*—Short. Rounded to truncate. Depressed.
- *Pistil point.*—Apical.

Skin:
- *Thickness.*—Medium.
- *Texture.*—Medium.
- *Tenacity.*—Tenacious to flesh.
- *Tendency to crack.*—None in dry season.
- *Down.*—Wanting.
- *Color.*—Red (7-L-6) shading to darker red (8-L-6).

Flesh:
- *Color.*—Red (7-L-6) with lighter streaking radiating from pit cavity.
- *Surface of pit cavity.*—Red (8-L-6).
- *Amygdalin.*—Wanting.
- *Texture.*—Firm. Fine. Crisp.
- *Fibers.*—Few. Fine.
- *Ripens.*—Evenly.
- *Flavor.*—Subacid.
- *Aroma.*—Wanting.
- *Eating quality.*—Best.

Stone:
- *Type.*—Semi-free.
- *Size.*—Medium. Average length — 1 cm. Average breadth — 8 mm. Average thickness — 7.5 mm.
- *Form.*—Globose — oval.
- *Base.*—Straight — oblique.
- *Hilum.*—Narrow. Oblong.
- *Apex.*—Rounded.
- *Sides.*—Equal.
- *Surface.*—Irregularly furrowed from base to apex ventrally. Ridged from base to apex.
- *Ridges.*—Jagged.
- *Ventral edge.*—Thick, with wing toward base.
- *Dorsal edge.*—Narrow.
- *Color.*—Beige (13-I-7).
- *Tendency to split.*—Slight in wet season.

Use: Market — local; dessert; shipping.
Keeping quality: Good.
Resistance to insects and diseases: Good.
Shipping quality: Good.
Variance in botanical details: The cherry tree and its fruit herein described may vary in slight detail due to climatic and soil conditions under which the variety may be grown; the present description being of the variety as grown in the Central Valley of California.

I claim:

1. A new and distinct variety of cherry tree substantially as illustrated and described; the fruit, in comparison to the Bing, is more globose in cross section, ripens more evenly and approximately six days earlier, sizes larger and holds to size with large crops, is of a more attractive glassy appearance, sugar is higher earlier, acid is mild, and the fruit rarely doubles.

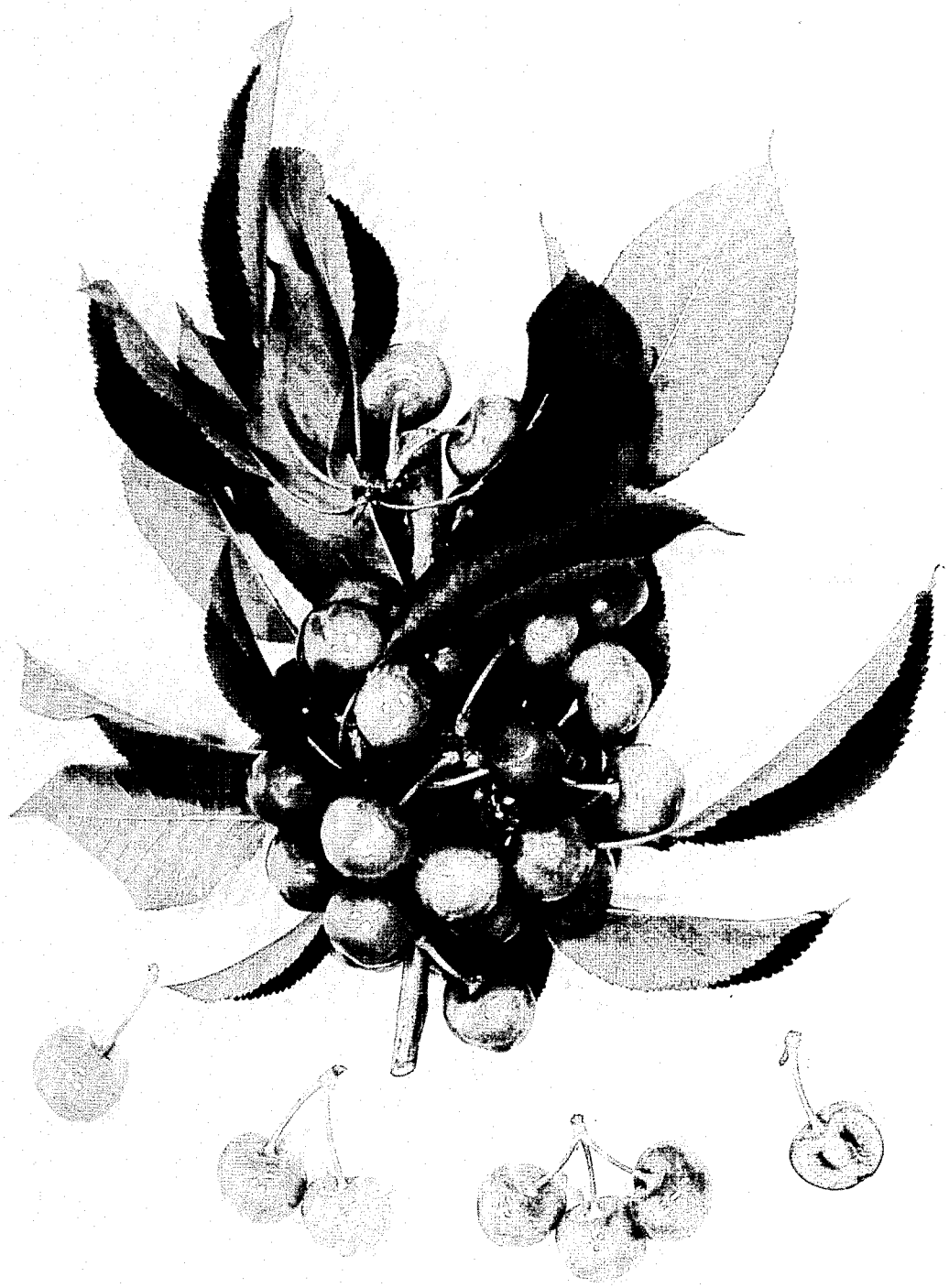

* * * * *